(12) United States Patent
Grafton (10) Patent No.: US 12,023,422 B1
(45) Date of Patent: Jul. 2, 2024

(54) UV AIR PURIFICATION SYSTEM

(71) Applicant: Matthew Grafton, St. Cloud, CA (US)

(72) Inventor: Matthew Grafton, St. Cloud, CA (US)

( * ) Notice: Subject to any disclaimer, the term of this patent is extended or adjusted under 35 U.S.C. 154(b) by 440 days.

(21) Appl. No.: 17/238,573

(22) Filed: Apr. 23, 2021

Related U.S. Application Data (60) Provisional application No. 63/107,074, filed on Oct. 29, 2020, provisional application No. 63/014,230, filed on Apr. 23, 2020.

(51) Int. Cl.
*A61L 9/20* (2006.01)
*B60H 3/06* (2006.01)

(52) U.S. Cl.
CPC ............. *A61L 9/20* (2013.01); *B60H 3/0658* (2013.01); *A61L 2209/12* (2013.01); *A61L 2209/16* (2013.01)

(58) Field of Classification Search
CPC .... A61L 9/20; A61L 2209/12; A61L 2209/16; B60H 3/0658
USPC ............................... 422/24, 120, 121; 96/224
See application file for complete search history.

(56) References Cited

U.S. PATENT DOCUMENTS

| | | | | |
|---|---|---|---|---|
| 5,997,619 | A * | 12/1999 | Knuth | B01D 46/0038 55/385.2 |
| 6,893,610 | B1 * | 5/2005 | Barnes | A61L 9/015 422/4 |
| 10,946,321 | B1 * | 3/2021 | Hamidzai | B01D 46/0028 |
| 2006/0005708 | A1 * | 1/2006 | Yuen | B03C 3/016 422/121 |
| 2011/0100221 | A1 * | 5/2011 | Wu | B01D 46/12 96/64 |
| 2011/0126828 | A1 * | 6/2011 | Wu | B03C 3/155 128/205.12 |
| 2019/0076558 | A1 * | 3/2019 | Zhang-Miske | B60Q 3/00 |
| 2019/0240371 | A1 * | 8/2019 | Benedek | B01D 53/8675 |
| 2020/0009283 | A1 * | 1/2020 | Gardner | A61L 9/20 |
| 2021/0046411 | A1 * | 2/2021 | Löfvendahl | B01D 46/0036 |
| 2021/0315749 | A1 * | 10/2021 | Uda | A61G 3/008 |
| 2022/0097491 | A1 * | 3/2022 | Brauer | A61L 9/20 |

FOREIGN PATENT DOCUMENTS

CN        208865343 U     *  5/2019

OTHER PUBLICATIONS

Machine-generated English translation of CN 208865343 U, published May 2019.*

* cited by examiner

*Primary Examiner* — Frank M Lawrence, Jr.
*Assistant Examiner* — Frank Lawrence
(74) *Attorney, Agent, or Firm* — Larry D. Johnson (57) ABSTRACT

A UV air purification system. In some implementations, the system includes a UV lamp housed in a module that can be installed in a vehicle anywhere that the vehicle's return air is accessible. In some implementations, the module includes a filter, and provides a UV light/cabin filter module that replaces the OEM filter in the return air duct in the vehicle. In other implementations, the module is installed in the vehicle's glove compartment or auxiliary recess.

9 Claims, 6 Drawing Sheets

UV AIR PURIFICATION SYSTEM

CROSS REFERENCE TO RELATED APPLICATIONS

The present application claims the benefit of the filing date of U.S. Provisional Patent Application Ser. No. 63/014,230, filed Apr. 23, 2020, and U.S. Provisional Patent Application Ser. No. 63/107,074, filed Oct. 29, 2020. The foregoing applications are incorporated by reference in their entireties as if fully set forth herein.

TECHNICAL FIELD

This written description relates generally to air purification systems, and more particularly to an improved ultraviolet (UV) air purification system for use in vehicles.

SUMMARY

Described below is a UV air purification system. In some implementations, the system includes a UV light fixture or lamp housed in a module that can be installed in a vehicle's HVAC return air path anywhere that the vehicle's return air is accessible, such that circulating air is exposed to the UV lamp to mitigate airborne bacteria, viruses, and mold. In some implementations, the module includes a filter. In some implementations, the module provides a UV light/cabin filter module that replaces the OEM filter in the return air duct in the vehicle. In other implementations, the module is installed in the vehicle's glove compartment. In some implementations, the glove compartment module is installed in an auxiliary recess in a vehicle's glove compartment, such as may ordinarily be used for storing the vehicle's owner's manual or the like.

In some implementations, the module includes grates or vents in one or more walls of the module. In some implementations, these grates or vents are placed in the top and bottom walls of the module. In some implementations, corresponding apertures are formed or cut in one or more corresponding walls of the vehicle's glove compartment assembly or auxiliary recess to enable air to flow from outside the glove compartment or auxiliary recess and around the UV lamp in the module.

In some implementations, air that has been treated by the UV lamp exits the module through an exhaust vent in a wall of the module. In some implementations, the exhaust vent is located on a rear wall of the module. In some implementations, the treated air is delivered from the exhaust vent to the evaporator of the vehicle's HVAC system.

In some implementations, the module is designed to mount in front of the vehicle's return air intake under the dash. In some implementations, when the vehicle's HVAC system is set to recirculate, all of the air in the vehicle is pulled through the module and exposed to ultraviolet radiation as it enters the vehicle's air intake.

In some implementations, a transformer for the UV lamp is located in the module. In some implementations, switching for the transformer and UV lamp is located in a separate control box. In some implementations, switching for the transformer and UV lamp is located in the vehicle's multiplex panel. In some implementations, switching for the transformer and UV lamp is located in a vehicle power point or cigarette lighter.

In some implementations, a plate or baffle may be positioned in the module to direct air flow.

In some implementations, the module includes a handle, grip, or other feature to facilitate insertion and removal of the module from the vehicle's glove compartment, auxiliary recess, or cabin filter compartment.

Particular embodiments of the subject matter described in this specification can be implemented so as to realize one or more of the following advantages.

In some implementations, the module can be installed anywhere in a vehicle where it can connect to the OEM return air of the vehicle. In some implementations, the module is installed in the front passenger cabin of a vehicle where it can connect to the OEM return air. In some implementations, the module replaces the vehicle's OEM cabin air filter.

In some implementations, the UV air purification system kills airborne bacteria, viruses, mold and other microorganisms in a vehicle.

In some implementations, the UV air purification system provides a compact and effective solution to improve air quality in vehicles, such as personal vehicles, commercial vehicles, ambulances, and other emergency vehicles.

The details of one or more embodiments of the subject matter described in this specification are set forth in the accompanying drawings and the description below. Other features, aspects, and advantages of the subject matter will become apparent from the description, the drawings, and the claims.

Those skilled in the art will appreciate that the conception upon which this disclosure is based readily may be utilized as a basis for the designing of other structures, methods and systems that include one or more of the various features described below.

Certain terminology and derivations thereof may be used in the following description for convenience in reference only, and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

DETAILED DESCRIPTION

Referring to FIGS. 1 through 12, wherein like reference numerals refer to like components in the various views, there is illustrated therein exemplary implementations of a UV air purification system.

Figure 1:
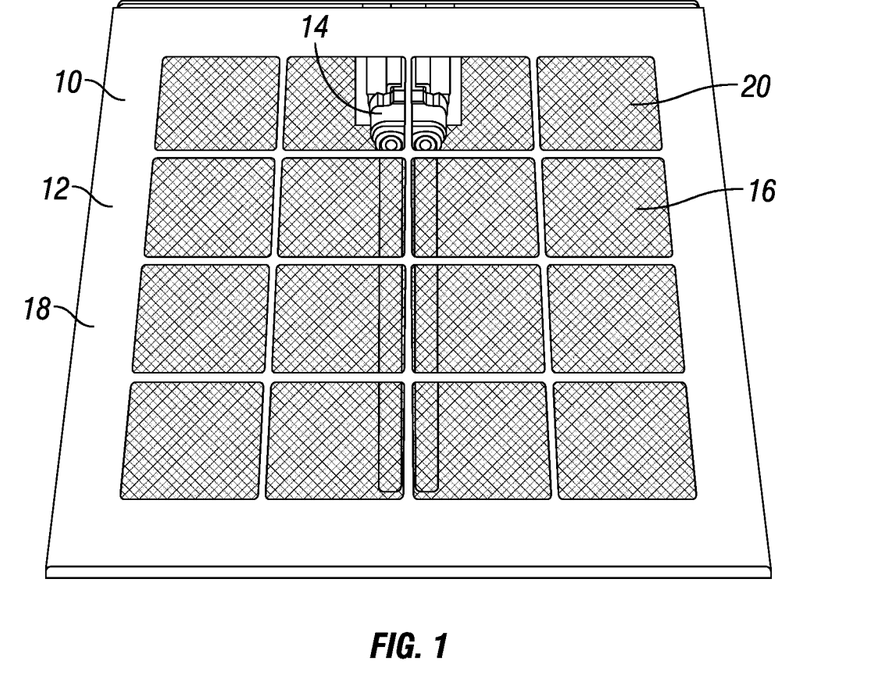
FIG. 1 is a top view of one implementation of a cabin filter module embodiment of a UV air purification system.

FIG. 1 is a top view of one implementation of a cabin filter module embodiment 10 of a UV air purification system, including enclosure 12 containing a UV lamp or light fixture 14 and filter media 16, with a top wall 18 bearing one or more grates or vents 20 permitting air passage through the module.

Figure 2:
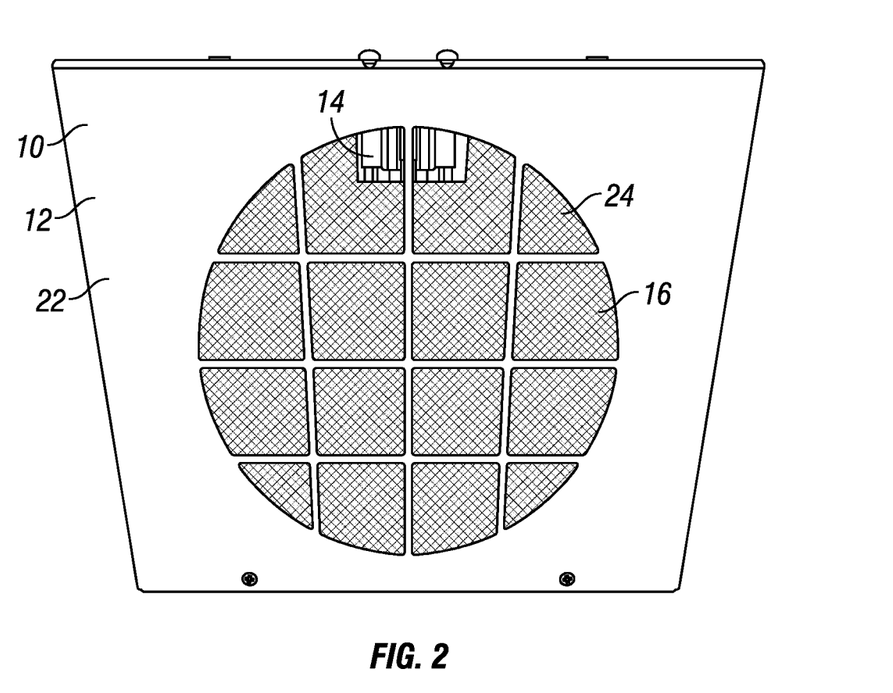
FIG. 2 is a bottom view thereof.

FIG. 2 is a bottom view of cabin filter module 10, including enclosure 12 containing a UV lamp or light fixture 14 and filter media 16, with a bottom wall 22 bearing one or more grates or vents 24 permitting air passage through the module.

Figure 3:
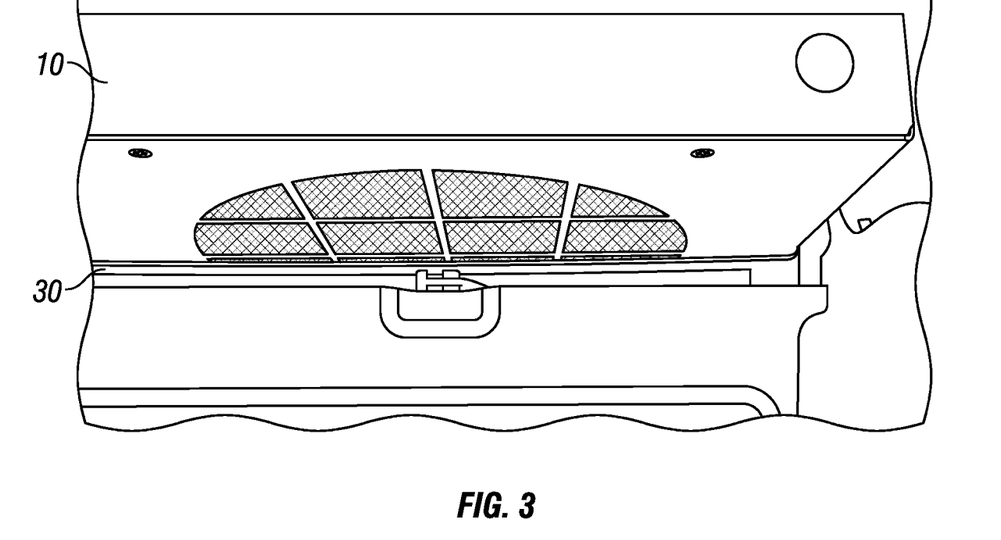
FIG. 3 is a view of one implementation of a cabin filter module partially installed into a vehicle's cabin filter compartment.

FIG. 3 is a view of one implementation of a cabin filter module 10 partially installed into a vehicle's cabin filter compartment 30.

Figure 4:
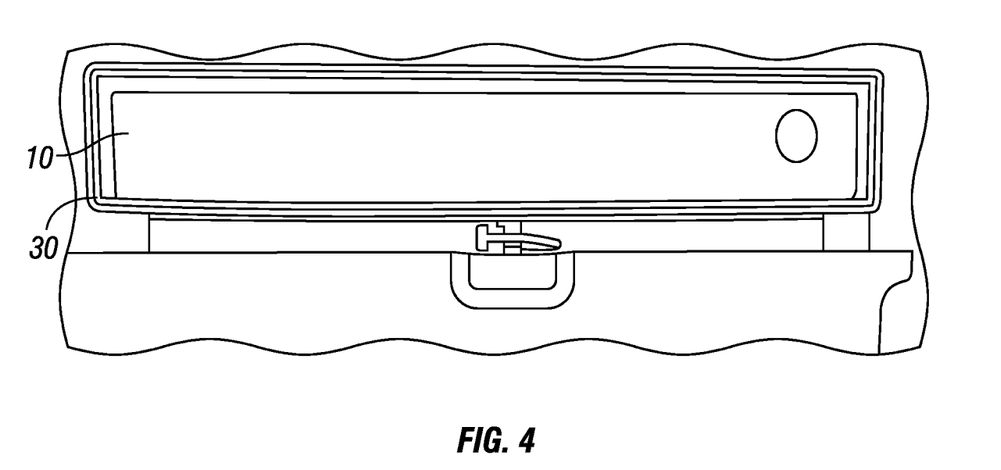
FIG. 4 is a view of the cabin filter module fully installed into a vehicle's cabin filter compartment.

FIG. 4 is a view of a cabin filter module 10 fully installed into a vehicle's cabin filter compartment 30.

In some implementations, the UV lamp produces ultraviolet radiation in the 253 nanometer wavelength, which has been shown to be effective in the destruction of many types of unwanted microorganism. In some implementations, the UV lamp is designed to provide over 8000 hours of useful ultraviolet radiation. A high efficiency U-tube lamp, coupled with a solid state ballast, is ideal for vehicular HVAC systems, and may require less than 2 amps at 12 volts. In some implementations, the module exposes all the air in a vehicle to ultraviolet radiation over 40 times each hour.

The module enclosure may be constructed from any appropriate material, and in the example implementations is constructed of metal. Other materials may also be used, such as plastic, for example.

Figure 5:
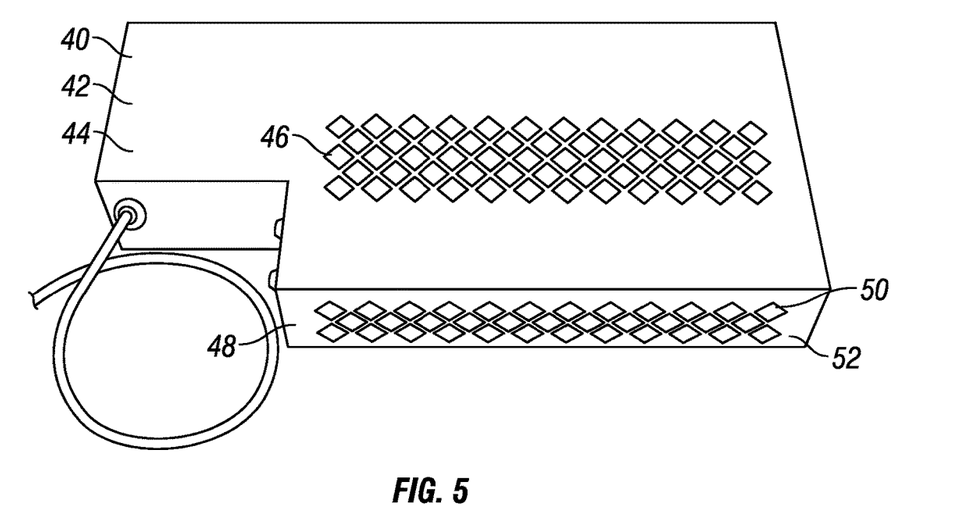
FIG. 5 is a view of one implementation of a glove compartment module embodiment of a UV air purification system, particularly for installation in an auxiliary recess of a vehicle's glove compartment.

FIG. 5 is a view of one implementation of a glove compartment module embodiment 40 of a UV air purification system, particularly for installation in an auxiliary recess of a vehicle's glove compartment. Module 40 includes enclosure 42 containing a UV lamp or light fixture (not visible in this view), with a bottom wall 44 bearing one or more grates or vents 46 permitting air passage into the module, and a rear wall 48 bearing one or more grates or vents 50 forming an exhaust vent 52.

Figure 6:
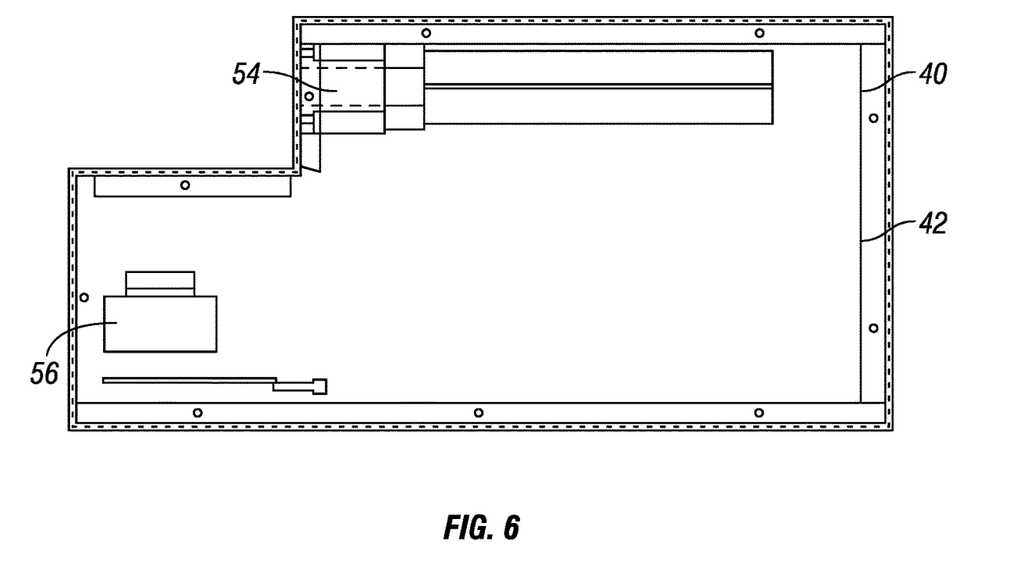
FIG. 6 is a cutaway view thereof.

FIG. 6 is a cutaway view of module 40, including enclosure 42 containing a UV lamp or light fixture 54 connected to transformer or electronic ballast 56.

In some implementations, the module is easily installed in a vehicle's existing equipment. In other implementations, the module is custom designed to fit into the dimensions of a particular vehicle's glove compartment or auxiliary recess.

Figure 7:
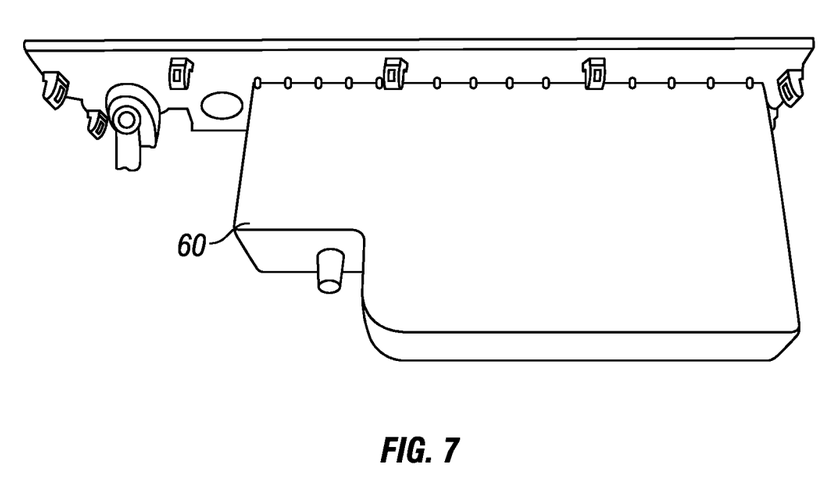
FIG. 7 is a view of a vehicle's glove compartment auxiliary recess assembly as removed from a dashboard or console of a vehicle.

FIG. 7 is a view of a vehicle's glove compartment auxiliary recess assembly 60 as removed from a dashboard or console of a vehicle.

Figure 8:
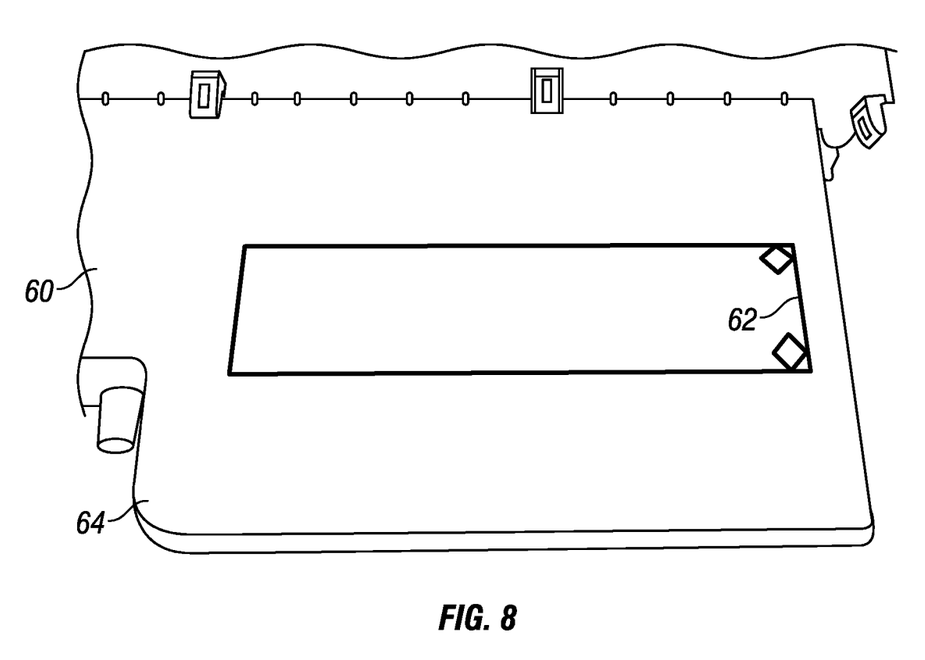
FIG. 8 is a view of markings having been placed on a bottom wall of a glove compartment auxiliary recess assembly to delineate the location of a return air opening to be cut in that wall.

FIG. 8 is a view of markings 62 having been placed on a bottom wall 64 of the glove compartment auxiliary recess assembly 60 to delineate the location of a return air opening to be cut in that wall.

Figure 9:
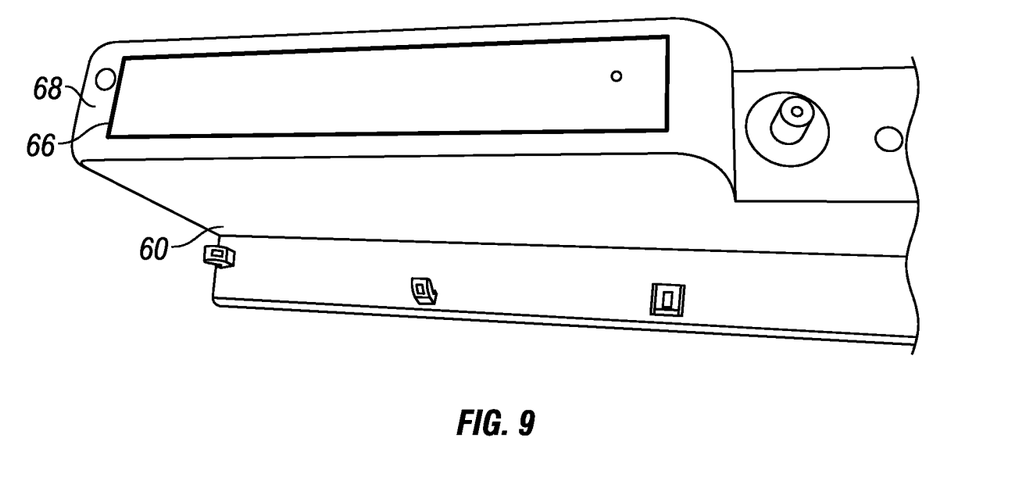
FIG. 9 is a view of markings having been placed on a rear wall of a glove compartment auxiliary recess assembly to delineate the location of an exhaust vent to be cut in that wall.

FIG. 9 is a view of markings 66 having been placed on a rear wall 68 of the glove compartment auxiliary recess assembly 60 to delineate the location of an exhaust vent opening to be cut in that wall.

Figure 10:
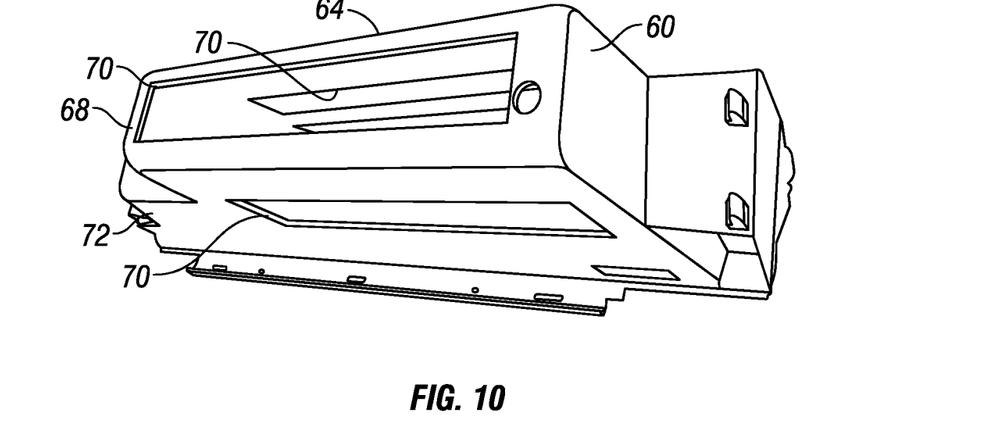
FIG. 10 is a view of openings having been cut in the top, bottom, and rear walls of a glove compartment auxiliary recess assembly.

FIG. 10 is a view of openings 70 having been cut in the bottom wall 64, rear wall 68, and top wall 72 of the glove compartment auxiliary recess assembly 60.

Figure 11:
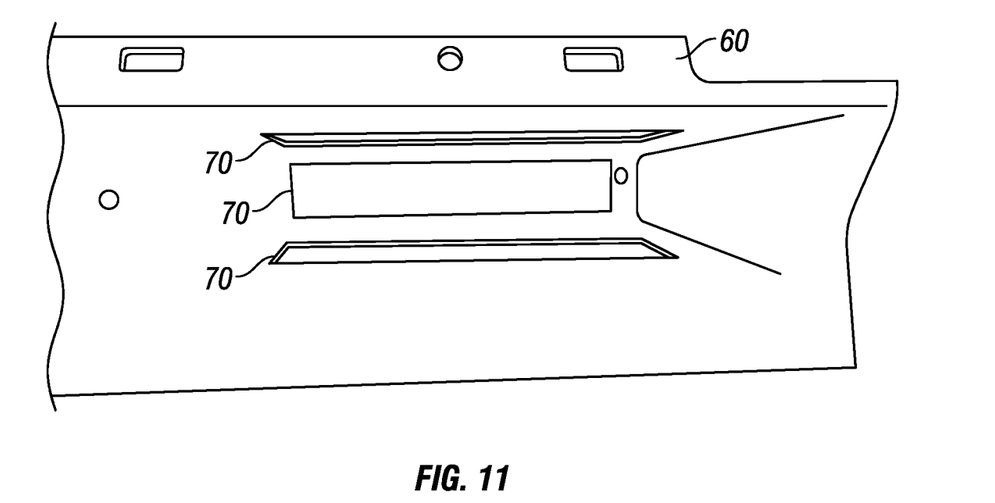
FIG. 11 is a front view the glove compartment auxiliary recess assembly showing the openings that have been cut in the top, bottom, and rear walls.

FIG. 11 is a front view the glove compartment auxiliary recess assembly 60 showing the openings 70 that have been cut in the top, bottom, and rear walls.

Figure 12:
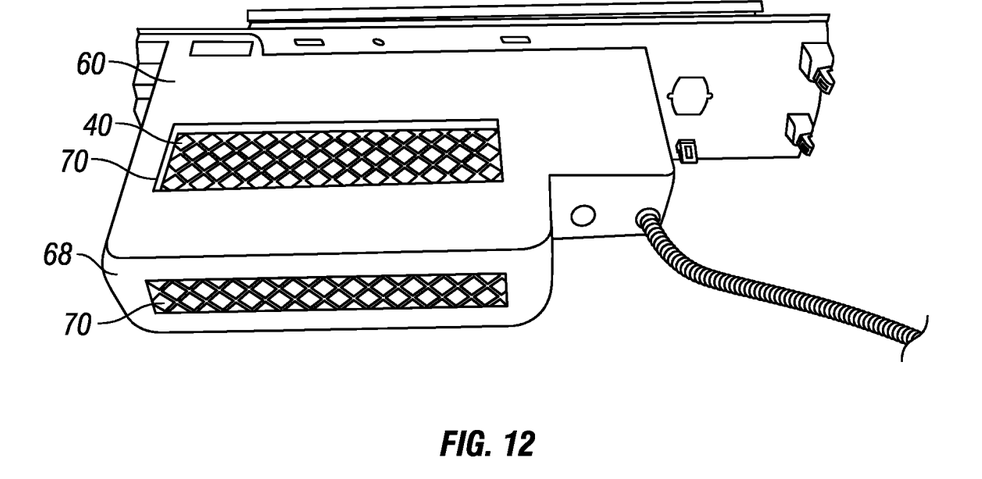
FIG. 12 is a rear view of a glove compartment module having been installed in a glove compartment auxiliary recess assembly.

FIG. 12 is a rear view of a glove compartment module 40 having been installed in the glove compartment auxiliary recess assembly 60. Once the assembly 60 is re-installed in the dashboard or console of a vehicle, return air can flow through openings 70 in the top and bottom walls of the assembly and into the module 40 to be treated by the UV lamp, and then exhausted from the module through the opening in the rear wall 68 of the assembly to the evaporator of the vehicle's HVAC system.

Ultraviolet radiation in the 253 nanometer wavelength (such as produced by the UV light fixture in some implementations of the UV air purification system described herein) has proven to be effective in the reduction or elimination of the following microorganisms:

Viruses: Filoviridae (Marburg Ebola), Poxviridae (Variola), Bunyaviridae (Hanta virus, Rift Valley fever), Arenaviridae (Lassa, Junin, etc.), Togaviridae (WEEV, VEEV), Flaviviridae (West Nile), Coronaviridae (COVID). Preliminary testing indicates that ultraviolet light may also be effective against the COVID-19 virus.

Bacteria: *Bacillus anthracis, B. megatherium* (veg.), *B. megatherium* (spores), *B. parathyphosus, B. subtilis* (spores), *Clostridium tetani, Corynebact diphtheriae, Eberthella typhosa, Escherichia coli, Leptospira* Spp. (Infectious jaundice), *Mycobacterium tuberculosis, Mycobacterium tuberculi, Neisseria catarrhalis, Phytomonas tumefaciens, Proteus vulgaris, Pseudomonas aeruginosa, Pseudomonas fluorescens, Salmonella enteritis, S. typhosa* (Typhoid fever), *S. paratyphi* (Enteric fever), *Sarcina lutea, Serratia marcescens, Shigella dysenteriae* (Dysentery form), *Shigella flexneri* (Dysentery form), *Shigella paradysenteriae, Spirillum rubrum, Staphylococcus albus, Staphylococcus aureus, Streptococcus haemolyticus, Streptococcus lactis, Streptococcus viridans*, Vibro comma-Cholera.

Yeasts: Common yeast cake, *Saccharomyces ellipsoideus, Saccharomyces cerevisiae, Torula sphaerica.*

Algae: Diatoms, Green algae, Blue algae.

Mould Spores: *Aspergillus amstelodami, Aspergillus flavus, Aspergillus glaucus, Aspergillus niger, Cladosporium herbarum, Mucor mucedo, Mucor racemosus, Oospora lactis, Penicillium digitatum, Penicillium expansum, Penicillium chrysogenum, Penicillium roqueforti, Rhizopus nigricans, Scopulriopsis bravicaulis.*

Typical instructions for installation of a glove compartment module in a vehicle (for example, in Ford F-250 and up vehicles from model years 2016 to 2021 with a passenger side multiple glove box design) may include the following:

First lower the glove box by removing the lever on the right side, then the pushing bumpers on each side inward, allowing the door to come down completely.

The UV light module will be mounted in the upper glove box housing, often used to contain the owner's manual. Remover the two screws and with a plastic prying tool gently pop that housing out. Disconnect the wires for the airbag and the light switch and the upper glove box is now ready to install the module.

Remove the lid from the module and use it to trace the return air grate locations on the top and bottom of the housing. Using the four corners of the grate create a rectangle that can be cut out using a utility knife. Do this to both sides.

Next cut a rectangle out of the rear of the housing. This is for the return air that passes across the UV light therefore purifying the cabin air. This cut out will be 7½" long and 1⅛" tall.

Next drill a ⅜" hole for the wires of the module to pass through the housing. This hole should be centered at ⅝" from the left side of the back of the housing.

After cutting all 3 return air grates out and drilling the hole for the wires, the module is ready to be put into the upper glove box housing. Check all return air cut outs for proper fitment. You should be able to see the grates in all openings. Pull the wires through the hole and press the unit in completely until it is flush with the front.

To control the module, we recommend that you use a 12V power source that is only hot when the A/C or Heat blower motor is on. You don't want the module on when the blower is turned off and there is no air being circulated. Also the vehicle must be on recirculate to force the air through the module and the UV light killing all germs and bacteria in the cabin.

Next install the upper glove box housing with module back in the vehicle and secure the glove box back to original operation.

Accordingly, the UV air purification system may be characterized as comprising a module including an enclosure containing a UV lamp, the enclosure having a top wall and a bottom wall each bearing one or more grates permitting air passage through the module, wherein when the module is installed in a vehicle's return air path, circulating air is exposed to the UV lamp to mitigate airborne bacteria, viruses, and mold.

In some implementations, the UV air purification system can be further characterized as including filter media. In some implementations, the UV air purification system can be further characterized as being installed in a vehicle's cabin filter compartment.

In other implementations, the UV air purification system can be characterized as including an enclosure having a rear wall bearing one or more grates forming an exhaust vent. In some implementations, the UV air purification system can be further characterized as being installed in a vehicle's glove compartment or auxiliary recess. In some implementations, the UV air purification system can be further characterized as being installed in a vehicle's glove compartment, wherein circulating air flows from outside the glove compartment and around the UV lamp in the module, and air that has been treated by the UV lamp exits the module through the exhaust vent and is delivered to an evaporator of the vehicle's HVAC system. In some implementations, the UV air purification system can be further characterized as wherein circulating air flows through openings in the vehicle's glove compartment adjacent the grates in the top wall and bottom wall of the enclosure. In some implementations, the UV air purification system can be further characterized as wherein circulating air flows from the module through the exhaust vent through an opening in the vehicle's glove compartment adjacent the grates in the rear wall of the enclosure.

In some implementations, the UV air purification system can be further characterized as including a transformer for the UV lamp located in the module.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

What is claimed as invention is:

1. A UV air purification system comprising:
    a module installed in a vehicle's glove compartment including an enclosure containing a UV lamp, the enclosure having a top wall and a bottom wall each bearing one or more grates permitting air passage through the module, and a rear wall bearing one or more grates forming an exhaust vent, wherein when the module is installed in a vehicle's return air path, circulating air is exposed to the UV lamp to mitigate airborne bacteria, viruses, and mold.

2. The UV air purification system of claim 1 wherein the enclosure includes filter media.

3. The UV air purification system of claim 1 wherein circulating air flows from outside the glove compartment and around the UV lamp in the module, and air that has been treated by the UV lamp exits the module through the exhaust vent and is delivered to an evaporator of the vehicle's HVAC system.

4. The UV air purification system of claim 1 wherein a transformer for the UV lamp is located in the module.

5. A UV air purification system comprising:
    a module installed in an auxiliary recess in a vehicle's glove compartment, the module including an enclosure containing a UV lamp, the enclosure having a top wall and a bottom wall each bearing one or more grates permitting air passage through the module, and a rear wall bearing one or more grates forming an exhaust vent, wherein when the module is installed in a vehicle's return air path, circulating air is exposed to the UV lamp to mitigate airborne bacteria, viruses, and mold.

6. The UV air purification system of claim 5 wherein the enclosure includes filter media.

7. The UV air purification system of claim 5 wherein circulating air flows from outside the glove compartment and around the UV lamp in the module, and air that has been treated by the UV lamp exits the module through the exhaust vent and is delivered to an evaporator of the vehicle's HVAC system.

8. The UV air purification system of claim 5 wherein circulating air flows from the module through the exhaust vent through an opening in the vehicle's glove compartment adjacent the grates in the rear wall of the enclosure.

9. The UV air purification system of claim 5 wherein a transformer for the UV lamp is located in the module.

* * * * *